US011603362B2

(12) United States Patent
Sølvhøj et al.

(10) Patent No.: US 11,603,362 B2
(45) Date of Patent: Mar. 14, 2023

(54) PROCESS FOR PREPARING GLYCOLIDE

(71) Applicant: HALDOR TOPSØE A/S, Kgs. Lyngby (DK)

(72) Inventors: Amanda Birgitte Sølvhøj, Værløse (DK); Rik De Clercq, Zandhoven (BE); Esben Taarning, Frederiksberg (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 126 days.

(21) Appl. No.: 17/287,138

(22) PCT Filed: Nov. 29, 2019

(86) PCT No.: PCT/EP2019/083086
§ 371 (c)(1),
(2) Date: Apr. 21, 2021

(87) PCT Pub. No.: WO2020/114905
PCT Pub. Date: Jun. 11, 2020

(65) Prior Publication Data
US 2021/0347753 A1    Nov. 11, 2021

(30) Foreign Application Priority Data
Dec. 6, 2018  (DK) .......................... PA 2018 00974

(51) Int. Cl.
C07D 319/12    (2006.01)
(52) U.S. Cl.
CPC .................. C07D 319/12 (2013.01)
(58) Field of Classification Search
CPC .................................................. C07D 319/12
See application file for complete search history.

(56) References Cited

U.S. PATENT DOCUMENTS

2013/0281733 A1    10/2013   Han et al.

FOREIGN PATENT DOCUMENTS

| CN | 106554342 A | | 4/2017 |
|---|---|---|---|
| JP | S53-46916 A | | 4/1978 |
| JP | 534451 | * | 11/2013 |
| WO | 02083661 A1 | | 10/2002 |
| WO | 2018095973 A1 | | 5/2018 |

OTHER PUBLICATIONS

Danish Search Report dated Jul. 3, 2019 by the Danish Patent Office in Application No. PA 2018 00974. (8 pages).
International Search Report (PCT/ISA/210) and Written Opinion (PCT/ISA/237) dated Jan. 29, 2020, by the European Patent Office as the International Searching Authority for International Application No. PCT/EP2019/083086. (9 pages).
J. Kua et al., "Glycolaldehyde Monomer and Oligomer Equilibria in Aqueous Solution: Comparing Computational Chemistry and NMR Data", The Journal of Physical Chemistry A, Mar. 11, 2013, pp. 2997-3008, vol. 117, dx.doi.org/10.1021/jp312202j, American Chemical Society Publications. (12 pages).
S. Tolborg et al., "Incorporation of Tin Affects Crystallization, Morphology, and Crystal Composition of SnBeta", Journal of Materials Chemistry A, Oct. 23, 2014, p. 20252-20262, No. 2, DOI:10.1039/c4ta05119j, Royal Society of Chemistry. (11 pages).

* cited by examiner

Primary Examiner — Valerie Rodriguez-Garcia
(74) Attorney, Agent, or Firm — Buchanan Ingersoll & Rooney P.C.

(57) ABSTRACT

According to the present invention a process is provided for producing glycolide which comprises contacting glycolaldehyde dimer with an oxidizing agent to produce a glycolide product. Preferably, the process is carried out in an aprotic environment, such as in a reaction mixture comprising the glycolaldehyde dimer, the oxidizing agent, the glycolide product and an aprotic solvent.

11 Claims, No Drawings

PROCESS FOR PREPARING GLYCOLIDE

FIELD OF THE INVENTION

The present invention regards a new process for preparing glycolide. The method uses glycolaldehyde dimer as a starting material.

BACKGROUND OF THE INVENTION

Glycolide is a valuable, commercially available compound, which is used e.g. as monomer/precursor for the production of the polymer Poly(Glycolic Acid), PGA.

PGA can be formed directly by polycondensation of glycolic acid, but this method is not preferred as it yields only low molecular weight polymers. Instead PGA is formed by ring-opening polymerization (ROP) of glycolide, which yields PGA of a much higher molecular weight.

The state of the art method for producing glycolide from glycolic acid entails two steps: the first step is a polycondensation of an aqueous glycolic acid solution to form low molecular weight PGA. This is achieved by heating glycolic acid to about 190° C. while reducing the pressure to 5 kPa in order to remove the water, which is also formed in the condensation reaction. The second step is a depolymerization reaction (also called a backbiting step) of the low molecular weight PGA to obtain the cyclic glycolide. This is achieved by heating the low Mw PGA; which is usually dissolved in a high-boiling solvent; to 250° C. under a reduced pressure of about 0.3 kPa. The formed glycolide is continuously distilled from the reaction mixture.

There is still a need for new and more simple and efficient methods for producing PGA, such as new and more efficient methods for producing the glycolide monomer. In particular, there is a need for new methods supporting production of PGA from sustainable, bio-based sources.

SUMMARY OF THE INVENTION

The state of the art method for producing the PGA precursor glycolide is a two-step process involving sub-atmospheric pressures and high temperatures. For industrial scale production, such process parameters increase costs for the process equipment, increase energy consumption and in general, require high stability of the compounds involved in the method.

The present inventors have now found a new process for producing glycolide which process is simple to perform, involves mild reaction conditions, and which may use bio-based resources as starting materials. The process uses glycolaldehyde (GA) dimer as reactant.

According to the present invention a novel process is provided for producing glycolide, which process comprises an oxidation step of contacting glycolaldehyde dimer with an oxidizing agent to produce a glycolide product.

The process according to the present invention has several advantages. The glycolaldehyde dimer is converted into glycolide in a single reaction step allowing it to be carried out in a single reactor. The reaction may be conducted under mild reaction conditions (e.g. atmospheric pressure, moderate temperature and pH). Even with a high starting concentration of glycolaldehyde dimer the yield and selectivity of glycolide is good. In addition, the reaction produces limited amounts of water. This is an advantage, since water must be removed before subjecting the glycolide to polymerization. Glycolaldehyde dimer can be obtained in a purified form, e.g. from renewable resources.

DETAILED DESCRIPTION OF THE INVENTION

It is known from the literature that glycolaldehyde in solution is unstable and exists as a complex mixture of up to nine different monomeric and dimeric forms which are in equilibrium with each other, of which one is glycolaldehyde dimer (Kua et. al., *J. Phys. Chem. A.* 2013, 117, 2997-3008). There is thus an intricate balance between the various forms of glycolaldehyde in solution.

The present inventors have now found that some of these reactions are in practice almost irreversible (or the reverse reaction is very slow) and they found a process for producing glycolide, which make use of this. Accordingly, the inventors have found that in solution the dissolved glycolaldehyde dimer (A), which has not yet been converted into glycolide, is in equilibrium with the glycolaldehyde monomer (B), whereas the conversion of glycolaldehyde monomer into glycolic acid and other byproducts is practically irreversible. This may be represented by the following reaction scheme:

Scheme 1 Reaction scheme illustrating the most important conversions of the glycolaldehyde dimer and its conversion products.

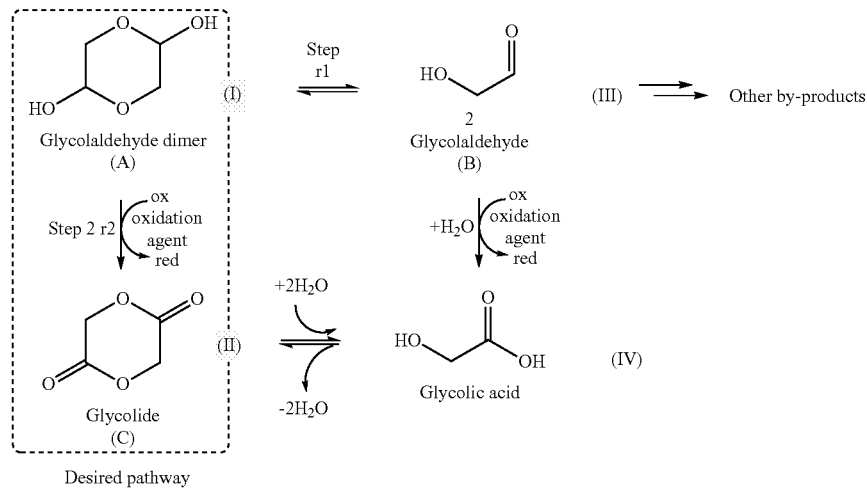

Accordingly, the inventors have now found that if the glycolaldehyde monomer is oxidized into glycolic acid etc. then it is no longer available for the conversion into first glycolaldehyde dimer and then glycolide. However, the inventors have also found that it is possible to select reaction conditions which favour the conversion of glycolaldehyde dimer into glycolide rather than the conversion of glycolaldehyde dimer into glycolaldehyde monomer and from there into e.g. glycolic acid. The inventors also found that the oxidation of glycolaldehyde dimer into glycolide is practically irreversible, and that therefore the glycolide formed does not inhibit further formation of glycolide through any reversible interactions. Since the monomerisation of glycolaldehyde dimer is reversible and the formation of glycolaldehyde monomer byproducts are practically irreversible, it is desirable to reduce the formation of such byproducts. Thus the yield of glycolide may be improved by selecting the reaction conditions such that the formation of glycolide is favoured over the monomerisation.

In other words, if the reversible monomerization step (1) occurs at a certain rate r1 and glycolaldehyde dimer (A) is irreversibly transformed to glycolide (C) in the presence of an oxidizing agent in an oxidation step (2) with a certain rate r2, the reaction conditions should preferably be selected such that the rate r2 is higher than the rate r1. This will result in net formation of glycolide (C) directly from glycolaldehyde dimer. The inventors have now found that the rates r1 and r2 for this reaction will vary with the reaction conditions, e.g. the choice of oxidizing agent, pH, the temperature, the concentration of protic compounds, and the choice of solvent. Accordingly, the present inventors have now found that glycolaldehyde dimer is a suitable starting material for producing glycolide. The process according to the present invention comprises an oxidation step of contacting glycolaldehyde dimer with an oxidizing agent to produce a glycolide product.

The process according to the present invention has the advantages of not requiring high or low pressures nor high temperatures and in addition the conversion of glycolaldehyde dimer to glycolide occurs in a single reaction step and thus it only requires a single reactor for carrying out the process according to the invention. In addition, suitable oxidation agents exist, which can oxidize glycolaldehyde dimer into glycolide under mild reaction conditions.

The term "glycolaldehyde dimer" (or "GA dimer") is meant to refer to the compound 1,4-Dioxane-2,5-diol, 2,5-Dihydroxy-1,4-dioxane of the formula I:

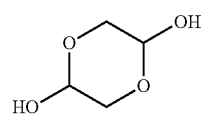

The glycolaldehyde dimer may also be referred to as hydroxyacetaldehyde dimer. The glycolaldehyde dimer can exist in three different conformations: A cis-isomer, where one hydroxy group is equatorial and the other hydroxy group is axial, and two different trans-isomers; one with both hydroxy-groups in equatorial positions and one with both hydroxy-groups in axial positions. Crystalline glycolaldehyde dimer has been shown to often exist in the trans-isomer form with all hydroxy-substituents in axial positions. Having a plane of symmetry, this conformation of glycolaldehyde dimer is a meso-form, despite the presence of two stereocenters. It is also referred to as a symmetrical glycolaldehyde dimer. In the present context the GA dimer may refer to GA dimer in its crystalline form (solid), in solution or partly dissolved, partly solid. When calculating amounts of GA dimer on weight basis, e.g. the amount of GA dimer measured out initially in an experiment, it is the amount of solid GA dimer added which is measured and noted, whether dissolved or not.

The term "glycolide" is meant to refer to the compound 1,4-dioxane-2,5-dione, 2,5-dioxo-1,4-dioxane of the formula II

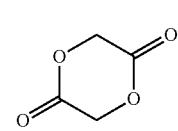

The term "oxidizing agent" (or "oxidation agent") is meant to refer to a compound which facilitates the oxidation of a substrate. This entails: Oxidation catalysts which function by employing molecular oxygen as the actual oxidant; oxidation catalysts which facilitate a hydrogen transfer from the substrate to a hydrogen acceptor present in the reaction mixture; oxidation catalysts which function by regenerating an oxidation reagent which is present in sub-stoichiometric amount; and oxidation reagents which are consumed on a stoichiometric basis in the oxidation process. Preferably, the oxidizing agent is capable of exerting its action at temperatures below 100° C., such as in the range of from 0-100° C., 20-80° C. or 30-60° C. According to an embodiment of the present invention, the oxidation step is carried out at temperatures below 100° C., such as in the range of from 0-100° C., 20-80° C. or 30-60° C.

The term "glycolide product" is meant to refer to the product obtained by carrying out the process according to the present invention. In addition to glycolide, it may e.g. contain solvent, unreacted glycolaldehyde dimer, any byproduct formed, any oxidizing agent still present etc., or it may be in a partly or completely purified form.

The inventors have found that the balance between the various forms of glycolaldehyde in solution is highly dependent on the nature of the solvent. For example, in an aqueous solution around 90% of the glycolaldehyde is on the form of the hydrated gem-diol, whereas a solution of glycolaldehyde in dimethylsulfoxide (DMSO) contains mainly a mixture of dimeric forms.

Accordingly, the present inventors have found that when carrying out the process according to the present invention in an aprotic environment the oxidation of glycolaldehyde dimer is favoured rather than the conversion of glycolaldehyde dimer into glycolaldehyde monomer and from the monomer into glycolic acid. According to an embodiment of the present invention, the oxidation step is carried out in an aprotic solvent.

An "aprotic environment" is meant to refer to an environment which has a very limited amount of reactive protons or of proton donor compounds available. In general the aprotic environment is provided as an aprotic liquid. An aprotic environment may be provided by carrying out the process according to the present invention in an aprotic solvent. However, small amounts of protic compounds may be present.

In the present context, an "aprotic solvent" is to be understood as a solvent lacking hydrogen atoms bound directly to atoms with a electronegativity higher than 2.6 on the Pauling scale such as, but not limited to, oxygen and nitrogen. An aprotic solvent is thereby not capable of forming hydrogen bonds to the solute (in this case glycolaldehyde dimer).

In the present context, a "protic compound" is to be understood as a compound which has hydrogen atoms bound directly to atoms with a electronegativity higher than 2.6 on the Pauling scale such as, but not limited to, oxygen and nitrogen, and which is therefore capable of donating hydrogen atoms to the solute or forming hydrogen bonds to the solute.

In an embodiment, the aprotic solvent is an oxo-compound. Solvents comprising oxo-compounds are generally aprotic.

In an embodiment of the present invention, the aprotic solvent is selected from the group consisting of N-methylpyrrolidone, dichloromethane, tetrahydrofuran (THF), ethyl acetate (EtOAc), acetone, methyl ethyl ketone, methyl isobutyl ketone, N, N-dimethylformamide (DMF), acetonitrile (MeCN), dimethyl sulfoxide (DMSO), propylene carbonate (PC), dioxane, and cyclohexanone; or mixtures thereof.

The protic compounds present in minor amounts may e.g. be water, any alcohol (such as methanol, ethanol, propanol, butanol etc.), any acid (such as formic acid, acetic acid, propanoic acid, glycolic acid etc.), and also the various forms of glycolaldehyde, such as glycolaldehyde monomer and glycolaldehyde dimer are protic compounds. Accordingly, it is desirable to limit formation of the various by-product forms of glycolaldehyde in the reaction mixture, since those will affect the tendency of the glycolaldehyde dimer to dissociate into the monomer rather than forming glycolide.

In an embodiment of the present invention, the aprotic solvent comprises less than 5 wt % water, preferably less than 1 wt % water. For the avoidance of doubt, in this embodiment the lower limit of water in the solvent is 0 wt %.

According to an embodiment of the present invention, the "contacting glycolaldehyde dimer with an oxidizing agent to produce a glycolide product" "in an aprotic solvent" will in general be carried out by mixing at least oxidizing agent, glycolaldehyde dimer and solvent to form a "reaction mixture". In the reaction mixture, the glycolaldehyde dimer is allowed to oxidize into the glycolide in the presence of the oxidizing agent. Accordingly the glycolide formed will also be part of the reaction mixture. Preferably the reaction mixture provides an aprotic environment, preferably by the presence of an aprotic solvent. Also various byproducts may be formed within the reaction mixture including glycolaldehyde monomer and glycolic acid. Any undissolved glycolaldehyde dimer present is also considered as part of the reaction mixture.

According to an embodiment of the present invention, minor amounts of protic compounds may be present in the reaction mixture. Accordingly, when "the oxidation step is carried out in an aprotic solvent", it is to be understood that up to 20 wt % of the reaction mixture may be made up of protic compounds; but preferably less than 15 wt %, 10 wt %, 5 wt % or 1 wt % of the reaction mixture is made up of protic compounds (including glycolaldehyde dimer, glycolaldehyde monomer or other forms of glycolaldehyde). For the avoidance of doubt, in this embodiment the lower limit of protic compounds in the reaction mixture is 0 wt %.

The inventors have found that glycolic acid, which is one of the byproducts formed when carrying out the invention, affect negatively the stability of glycolaldehyde dimer in particular due to its protic nature. In an embodiment of the present invention, the reaction mixture comprises less than 10 wt % glycolic acid, preferably less than 5 wt % or less than 1 wt % glycolic acid. For the avoidance of doubt, in this embodiment the lower limit of glycolic acid in the reaction mixture is 0 wt %.

In an embodiment of the present invention, the aprotic solvent makes up at least 70 wt %, such as at least 80, 90, 95, or 98 wt % of the reaction mixture.

The glycolaldehyde dimer may have limited solubility in some of the aprotic solvents and a part of the glycolaldehyde dimer may thus be present in the reaction mixture on solid form. In an embodiment of the present invention, the concentration of dissolved glycolaldehyde dimer in the liquid phase of the reaction mixture is below 60 g/l (1M), preferably below 30 g/l (0.5 M), such as in the range of from 60 g/l (1M) to 3 g/l (0.05M) or from 30 g/l (0.5M) to 6 g/l (0.1M). If the process according to the present invention is carried out in a batch or a fed batch process, the concentrations given refer to the initial concentration of glycolaldehyde dimer in the liquid phase. Accordingly, the total amount of glycolaldehyde dimer in the reactor may be higher than the amount dissolved in the reaction mixture. In such case solid glycolaldehyde dimer may gradually dissolve as glycolaldehyde dimer is converted into glycolide.

In an embodiment of the present invention the reaction mixture consists of a liquid phase in contact with undissolved, solid glycolaldehyde dimer. The solid undissolved glycolaldehyde dimer will dissolve gradually as solvated glycolaldehyde dimer is converted into glycolide. This way the concentration of GA dimer in solution is kept constant while the concentration of glycolide slowly increases.

This is an advantage since the solid glycolaldehyde dimer is not converted to the GA monomer until it is dissolved, and thus a lower amount of oxidizing agent is necessary.

Generally, the reaction mixture forms a zone, which may be referred to as a reaction zone. The reaction zone may e.g. be delimited by reactor walls.

In an embodiment according to the present invention, the glycolaldehyde dimer is fed to the reaction or the reaction mixture or the reaction zone as the symmetrical glycolaldehyde dimer. According to an embodiment of the present invention, the glycolaldehyde dimer is fed to the reaction or the reaction mixture or the reaction zone as solid glycolaldehyde dimer.

The glycolide dimer may be derived from a bio-based resource. When bio-based resources are used as raw materials for producing glycolaldehyde dimer, the $^{14}C$ content will in general be above 0.5 parts per trillion of the total carbon content.

In an embodiment according to the present invention, the oxidizing agent is selected from the group consisting of Dess-Martin periodinane, peracetic acid, oxygen, hydrogen peroxide, Oppenauer oxidation catalysts, metallo silicates, Shvo's catalyst, aluminum isopropoxide; or mixtures thereof.

The term "Shvo's catalyst" is meant to refer to a compound of the formula $C_{62}H_{42}O_6Ru_2$ (CAS no 104439-77-2). It is an organoruthenium compound that is used as transfer hydrogenation catalyst. Related known derivatives where p-tolyl replaces some of the phenyl groups is meant to be included in this term.

The term "Dess-Martin periodinane" is meant to refer to the compound of the formula $C_{13}H_{13}IO_8$ (CAS no 87413-09-0). It is a chemical reagent used to oxidize primary alcohols to aldehydes and secondary alcohols to ketones.

The term "Oppenauer oxidation catalyst" is meant to refer to any compound which catalyzes an Oppenauer oxidation or a Meerwein-Pondorff-Verley reduction, collectively known as MPVO-reactions. By MPVO reactions are understood reactions in which a secondary alcohol is oxidized to a ketone by hydrogen transfer to a suitable ketone, which is correspondingly transformed into a secondary alcohol. This includes in particular any compound of the formula $Al(OR)_3$ where R=alkyl or aryl substituent C1-C20 containing no or some heteroatoms selected from O, N, S, Cl, Br, I, or mixtures thereof.

The term "metallo silicate" (also known as metallo silicate material, metallo silicate composition or metallo silicate catalyst) is meant to refer to one or more solid materials comprising a silicon oxide structure and an active metal and/or metal oxide components, wherein the active metal and/or metal oxide components are incorporated into and/or grafted onto the surface of the silicon oxide framework structure (i.e. the silicon oxide structure comprises M-O—Si bonds). The silicon oxide framework structure is also known as a silicate. Metallo silicate materials may be crystalline or non-crystalline. Non-crystalline metallo silicate materials include ordered mesoporous amorphous or other mesoporous amorphous forms. Crystalline microporous material includes zeolite materials and zeotype materials. According to an embodiment of the present invention, the metallo silicate material has a zeolite framework structure, which is selected from the group consisting of BEA, MFI, FAU, MOR, FER and MWW. In an embodiment, the metallo silicate has the mesoporous framework structure MCM-41 and SBA-15.

Zeolite materials are crystalline aluminosilicates with a microporous crystalline structure, according to Corma et al., Chem. Rev. 1995, 95 pp 559-614. The aluminum atoms of the zeolite material may be partly or fully substituted by an active metal; these materials fall within the class of zeotype materials. For the purpose of this application zeotype materials encompass zeolite materials and the metallo silicate material may be substituted with an active metal imparting Lewis acidity to the material. Metallo silicate materials act as an electron pair acceptor to increase the reactivity of a substrate. According to an embodiment of the present invention, the metallo silicate material comprises an active metal selected from one or more of the groups consisting of Al, Sn, Ti, Pb, Zr, Zn, V, Nb, Ta, Ge and Hf, preferably from Sn, Zr, Ge and Hf, more preferred it is Sn.

According to an embodiment of the present invention, the metallosilicate material is Sn-BEA, Sn-MCM-41 or a soluble tin salt. The soluble tin salt may be selected from the group consisting of tin chloride ($SnCl_4$ and $SnCl_2$), tin fluoride ($SnF_4$ and $SnF_2$), tin bromide ($SnBr_4$ and $SnBr_2$), tin iodide ($SnI_4$ and $SnI_2$), tin acetylacetonate ($Sn(C_5H_7O_2)_2$), tin pyrophosphate ($Sn_2P_2O_7$), tin acetate ($Sn(CH_3CO_2)_4$ and $Sn(CH_3CO_2)_2$), tin oxalate ($Sn(C_2O_4)_2$ and $SnC_2O_4$), tintriflate ($Sn(CF_3SO_3)_2$ and $Sn(CF_3SO_3)_4$) The corresponding salts of e.g. Al, Ti, Pb, Zr, Zn, V, Nb, Ta, Ge and Hf will also be suitable for use as oxidizing agent.

In an embodiment according to the present invention, the oxidation step is carried out at moderate temperatures. Accordingly, the oxidation step is preferably conducted at a temperature in the range of from 0-100° C., such as in the range of from 20-80 or 30-60° C. Carrying out the invention at such temperatures has several advantages. First of all, it is more economical to run an industrial scale process at lower temperatures. Secondly, the risk of decomposition of the unstable compounds present, such as glycolaldehyde monomer and glycolaldehyde dimer, is lower at lower temperatures. In an embodiment according to the present invention, the oxidation step is carried out at a temperature below the melting point of the glycolaldehyde dimer. The melting point of the glycolaldehyde dimer is around 80-90° C. This has an advantage that the equilibrium is kept closer towards the dimer than the monomer. In addition, the less glycolaldehyde dimer which is dissolved, the shorter the residence time is for the dimer in the solution and thus, less dimer is likely to monomerize spontaneously. This will also favor the conversion into glycolide. Accordingly a reaction temperature below 80° C. is advantageous, and a combination of a reaction temperature below 80° C. and a pressure near atmospheric pressure is advantageous.

According to an embodiment of the present invention, the oxidation step is carried out in liquid phase. According to an embodiment of the present invention, the oxidation step is carried out at atmospheric pressure. According to an embodiment of the present invention, the oxidation step is carried out close to atmospheric pressure and at a temperature in the range of from 20-80 or 30-60° C.

The oxidation step may be performed in batch mode. Here, glycolaldehyde dimer, an oxidizing agent and a solvent are contacted to form a reaction mixture in a reaction vessel where they can be mixed thoroughly and the temperature is controlled at the desired level. They are kept in this vessel for a sufficient time to transform glycolaldehyde dimer into glycolide. The reaction vessel is then emptied by recovering the reaction mixture. Optionally the glycolide may be purified from the reaction mixture, e.g. by distillation, ion exchange, chromatography, evaporation, precipitation or recrystallization.

The oxidation process may alternatively be performed as a continuous process, for instance using a continuously stirred tank reactor (CSTR). In this case, glycolaldehyde dimer, an oxidizing agent and a solvent is added to a reaction vessel at more or less the same rate as product is withdrawn from the reaction vessel. Accordingly, a continuous reactor in general comprises one or more inlets and one or more outlets and stirring means within the reactor. A continuous process has advantages for industrial scale production of glycolide, since in general it is less work intensive to run and does not have periods without producing. Also, a tendency to degradation (dissociation) of glycolide with time has been observed. A further advantage of using a CSTR reactor is that the time the reaction mixture and in particular the feed is in the reaction zone is kept short.

In an embodiment according to the present invention, the oxidation step is conducted as a continuous process.

In the present context, the term "continuous process" is to be understood as a process where a feed stream comprising glycolaldehyde dimer is fed to a reaction mixture or a reaction zone comprising aprotic solvent, oxidizing agent as well as glycolaldehyde dimer which is being consumed and glycolide, which is being formed. In the reaction mixture/reaction zone, the glycolaldehyde dimer is allowed to oxidize into the glycolide in the presence of the oxidizing agent and in the aprotic environment provided by the aprotic solvent. A product stream comprising the glycolide is recovered from the reaction mixture/reaction zone. The feed stream and the product stream optionally comprises aprotic solvent and/or oxidizing agent.

In an embodiment of the present invention, the pH of the reaction mixture is kept in the range of from 6 to 8.

The inventors have found that the conversion of glycolaldehyde dimer into glycolide is much faster than the dissociation of glycolide into glycolic acid. Therefore it is an advantage to facilitate short reaction times. In an embodiment of the present invention the oxidation step is carried out for a period of time in the range of from 0.1 minute to 48 hours, such as in the range of from 1 minute to 24 hours or from 5 minutes to 2 hours.

In an embodiment of the present invention, the glycolide is recovered e.g. by precipitating it directly from the reaction mixture by cooling and collecting the solid glycolide precipitate. The glycolide may be purified further by washing or by recrystallization.

Any water present in the reaction mixture may be evaporated.

The purified glycolide obtained from the process according to the present invention may be used in the same way as the commercially available glycolide, e.g. for producing PGA.

EXAMPLE

Example 1: Stability of Glycolide

1a: Stability by Gas Chromatography (GC)

In a 100 ml round bottomed flask was placed 50 ml solvent (acetone or 1,4-dioxane), and 500 mg glycolide was added to the flask together with 100 mg of naphthalene (internal standard). The flask was equipped with a water-cooled condenser and the flask was heated in an oil bath, set at a temperature that allows the reaction mixture to boil (usually 10° C. above the boiling temperature of the chosen solvent). The effective reaction temperature in the flask is thus the boiling temperature of acetone (56° C.) or 1,4-dioxane (101° C.) respectively. The mixture was refluxed for 150 minutes, after which 1 ml of water (2 vol %) was added to the flask. After an additional 120 minutes, 50 mg of glycolic acid (10 wt % compared to glycolide), dissolved in an additional 1 ml of water, were added to the mixture. The final reaction mixture was then refluxed for another 2 hours.

Intermediate samples were taken and analyzed by GC. The concentration of glycolide was determined by a calibration curve using naphthalene as the internal standard. The glycolide recovery (%) is defined as the amount of glycolide in the reaction mixture compared to the initial amount of glycolide added to the flask.

See the results in table 1 below:

TABLE 1

Stability of glycolide

| Solvent, temperature | Glycolide recovery (%) | | | | | |
|---|---|---|---|---|---|---|
| | No protic compound | | 2 vol % $H_2O$ | | 4 vol % $H_2O$, 10 wt % glycolic acid | |
| | 30 min | 130 min | 160 min | 250 min | 300 min | 360 min |
| Acetone, 55° C. | 100 | 99.5 | 99.4 | 98.0 | 94.5 | 91.5 |
| Dioxane, 101° C. | 100 | 99.9 | 99.7 | 97.3 | 93 | 81 |

1b: Stability of Glycolide by NMR

The stability of glycolide in acetone at various conditions was assessed by NMR.

In acetone at 45° C. the glycolide seems completely stable, and no other peaks appear during the approximately 90 minutes the sample is run for. Even in the presence of 5% (v/v) water in the solvent, which speeded up the monomerization of the glycolaldehyde dimer considerably, the compound seems very stable. The presence of acid (1% (w/w) glycolic acid in acetone with water (5 v/v %)) changes the picture completely, and the transformation of glycolide into glycolic acid is more or less completed within the course of four hours.

Example 2: Stability of Glycolaldehyde Dimer

Glycolaldehyde in solution exists as an equilibrium between several different monomeric and dimeric forms. These are described and numbered by Kua et al. (Kua et. al., J. Phys. Chem. A. 2013, 117, 2997-3008). A schematic overview with numbers is shown below. The solid glycolaldehyde dimer is comprised only of the symmetric dimeric form (1). This is the trans-form that has the hydroxyl groups positioned axially.

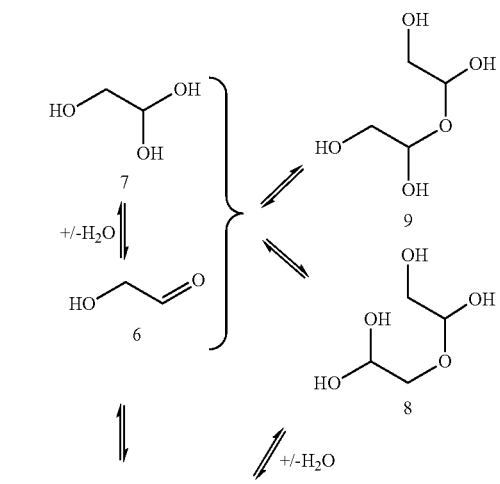

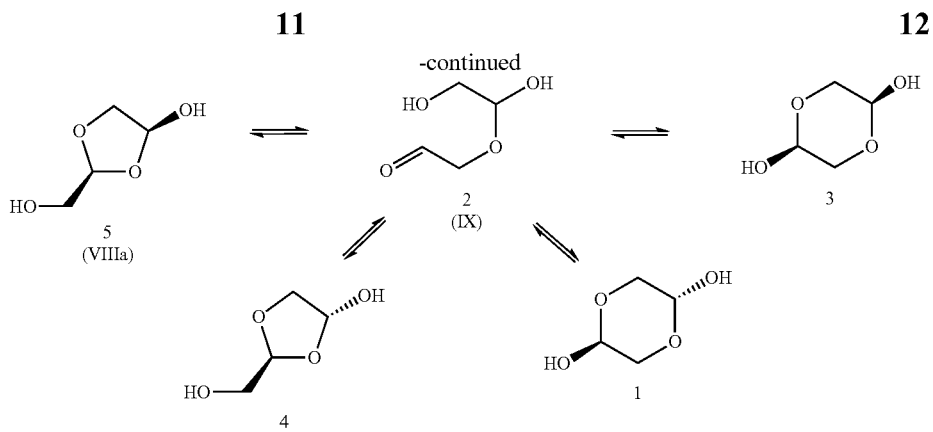

Experiment

The monomerization rate of the symmetric glycolaldehyde dimer (1) in various solvents and at different temperatures was assessed by dissolving 10 mg glycolaldehyde dimer in 1 ml solvent and running NMR of the solution over time.

Conclusion:

In acetone at room temperature the dimer (1) is very stable. Slow equilibration between this and other dimeric forms (3, 4 & 5) is observed, but even after 4 hours the dominant species by far is the symmetric dimer (1). The sample was left running for ~16 hours, at which point the temperature was raised to 40° C. At this temperature the rate of the equilibration is increased, but still slow and remains mainly an equilibrium between dimeric forms.

With the presence of 5% (v/v) water in the acetone solvent, the equilibration occurs much more rapidly, and already after approximately one hour the amount of the symmetrical dimer (1) is reduced to about half of the initial concentration. The formed species are still primarily other cyclic dimeric forms (3, 4 & 5). When pure water is used as solvent, the equilibrium between the different dimeric forms is reached within minutes after the experiment is started. From here is observed the gradual increase in the hydrated glycolaldehyde monomer (7), followed by a slow decrease in the concentration of the different dimeric forms.

The presence of acid has a strong effect on monomerisation: With 1% (w/w) glycolic acid in the acetone/water mixture, the equilibrium has been reached already before the NMR experiment is started.

In dioxane at room temperature the dimer is also quite stable, although a gradual decrease in the concentration can be seen. At 40° C. the decrease of dimer is considerable, and already after approximately one hour the concentration of the symmetrical dimer is less than half of the initial. At 60° C. the equilibrium seems to be settled already before the measurement starts.

Example 3: Conversion of Glycolaldehyde Dimer into Glycolide with Dess Martin Periodinane as Oxidizing Agent In a 25 ml round bottomed flask was placed 428 mg Dess Martin Periodinane (DMP; 1.00 mmol) and 5 ml acetone as solvent. 104 mg GA dimer (0.87 mmol) was added to the flask, and the resulting reaction mixture was subjected to stirring at room temperature. Samples were taken after 1 h, 2 h and 18 h respectively.

Each sample of the reaction mixture was analyzed by GC in the following way:

The reaction mixture was transferred to a volumetric flask and diluted to an exact volume. A sample from the resulting solution was filtered through a syringe filter (0.45 um membrane) into a GC vial and analyzed on a GC. The results were compared with a standard of commercially available glycolide in the same solvent.

See results in table 2 below.

After 1 hour the concentration of acetic acid was 32.7 g/L indicating that all of the DMP had reacted with the GA dimer after 1 hour (2 moles of acetic acid formed per mol of DMP consumed).

TABLE 2 conversion of GA dimer in g/L and mol % (mol of compound per mol of GA dimer added)

| | Time | | | | | |
|---|---|---|---|---|---|---|
| | 1 h | | 2 h | | 18 h | |
| | Unit | | | | | |
| | g/L | mol % | g/L | mol % | g/L | mol % |
| GA dimer | 12.66 | 61 | | | | |
| Glycolide | 2.41 | 12 | 2.10 | | 1.04 | |
| Glycolic acid | 3.59 | 14 | | | | |
| Acetic acid | 32.7 | — | | | | |

Conclusion: Some degradation of the glycolide product seems to occur with increasing time, and it seems possible that even shorter reaction times would be beneficial for achieving a higher yield of glycolide. It is hypothesized that glycolide is in equilibrium with glycolic acid. This could explain the disappearance of glycolide with time.

Example 4: Conversion of Glycolaldehyde Dimer into Glycolide with Peracetic Acid as Oxidizing Agent To a stirring solution of 0.1623 g GA dimer, 0.1025 NaBr, 0.0375 g Co(OAc)$_2$ and 6 ml acetone (solvent) in a 25 ml two-necked round-bottomed flask was added 0.5 ml of a 35 wt % solution of peracetic acid (AcOOH). The resulting reaction mixture was refluxed for 18 hours.

A sample of the reaction mixture was analyzed by GC in the same way as explained in example 3. Furthermore, a sample was analyzed on HPLC. The analyses showed a 81% conversion of glycolaldehyde along with a formation of glycolide of 1.3% and glycolic acid formation of 3.3%.

Example 5: Conversion of Glycolaldehyde Dimer into Glycolide with Tin-Beta-Zeolite as Oxidizing Agent In a 20 ml ace-vial was placed 3 ml acetone as solvent, 0.0662 g GA dimer and 0.018 g tin-beta-zeolite (Using Sn-Beta (Si/Sn=200) prepared following the fluoride-route according to S. Tolborg et. al., Journal of Materials Chemistry A, 47, 2014, 2, 20252-20262)). The resulting reaction mixture was heated to 100° C. under stirring overnight (about 18 hours).

A sample of the reaction mixture was analyzed by GC in the same way as explained in example 3. The sample showed formation of glycolide in 3% yield.

Example 6: Conversion of Glycolaldehyde Dimer into Glycolide with Shvo's Catalyst as Oxidizing Agent in Various Solvents and with Various Catalyst Loadings

Example 6A: Acetone as Solvent

In a Schlenk flask was placed 0.0596 g GA dimer and 0.0139 g Schvo's catalyst. The flask was evacuated and purged with $N_2$ three times. 6 ml acetone was added via a syringe and the reaction mixture was heated to 50° C. under $N_2$ for 3 hours.

Samples of the reaction mixture were analysed by GC in the same way as explained in example 3. The GC analysis results are shown in table 3 below.

Example 6B: Cyclohexanone as Solvent

In a Schlenk flask was placed 0.0788 g GA dimer and 0.0142 g Schvo's catalyst. The flask was evacuated and purged with $N_2$ three times. 6 ml cyclohexanone was added via a syringe and the reaction mixture was heated to 75° C. under $N_2$ for 2 hours.

Samples of the reaction mixture were analyzed by GC in the same way as explained in example 3, furthermore, a sample was taken for NMR. The GC analysis results are shown in table 3 below. The NMR analysis confirmed the presence of glycolide in 3.5 g/l concentration.

Example 6C: Cyclohexanone as Solvent and Increased Catalyst Loading

In a Schlenk flask was placed 0.0687 g GA dimer and 0.0221 g Schvo's catalyst. The flask was evacuated and purged with $N_2$ three times. 6 ml cyclohexanone was added via a syringe and the reaction mixture was heated to 75° C. under $N_2$ for 2 hours.

A sample of the reaction mixture was analyzed by GC in the same way as explained in example 3. The GC analysis results are shown in table 3 below.

Example 6D: Methanol as Solvent (Protic Solvent)

In a Schlenk flask was placed 0.0788 g GA dimer and 0.0142 g Schvo's catalyst. The flask was evacuated and purged with $N_2$ three times. 6 ml methanol (solvent) and 0.5 ml acetone (hydrogen acceptor) was added via a syringe and the reaction mixture was heated to 65° C. under $N_2$ for 3 hours.

A sample of the reaction mixture was analyzed by GC in the same way as explained in example 3. The GC analysis results are shown in table 3 below.

TABLE 3

| Example | 6A | 6B | 6C | 6D |
|---|---|---|---|---|
| Catalyst loading | 1.29 mol % | 0.98 mol % | 1.7 mol % | 1.00 mol % |
| Initial GA dimer concentration | 9.9 g/l | 13.2 g/l | 11.5 g/l | 12.0 g/l |
| Reaction temperature | 50° C. | 75° C. | 75° C. | 65° C. |
| Solvent | acetone | cyclohexanone | cyclohexanone | Methanol |
| Sample time (reaction time) | 3 h | 2 h | 2 h | 3 h |
| Yield of glycolide (GC analysis) | 9.7% | 29% | 28% | 0% |

Conclusion to the experiments employing Shvo's catalyst as oxidizing agent: Glycolide is formed in considerable amounts. When the solvent is changed from acetone to cyclohexanone the yield increases, which may be attributed to the increased reaction temperature. Increasing the catalyst loading does not seem to have a positive effect on the yield, and neither does increasing the reaction time. In all the examples the reaction was run over at least 18 hours and samples taken continuously, but in all cases the first sample contained the highest amount of glycolide.

When the oxidation reaction is run in a protic solvent, the monomerization of GA dimer to monomer (1) is faster than the oxidation of GA dimer to glycolide (2). This can be concluded from the observations that when running the reaction in cyclohexanone solvent it results in the formation of glycolide (29%), whereas running the reaction in methanol (+7% acetone as hydrogen acceptor) it results in the formation of methyl glycolate in around 80% yield. In both cases unreacted glycolaldehyde make up the remaining percentages.

The methyl glycolate is formed through an initial monomerization of glycolaldehyde dimer (A) to form the glycolaldehyde monomer (B), followed by formation of a hemiacetal between methanol and the glycolaldehyde monomer and a subsequent oxidation of the hemiacetal to form methyl glycolate. Thus, the formation of methyl glycolate proves the presence of the glycolaldehyde monomer.

The invention claimed is:

1. A process for producing glycolide comprising an oxidation step of contacting glycolaldehyde dimer with an oxidizing agent to produce a glycolide product, wherein the oxidation step is carried out in an aprotic solvent.

2. The process according to claim 1, wherein the oxidation step is carried out in a reaction mixture comprising the glycolaldehyde dimer, the oxidizing agent, the glycolide product and the aprotic solvent.

3. The process according to claim 1, wherein the aprotic solvent makes up at least 70 wt % of the reaction mixture.

4. The process according to claim 1, wherein the aprotic solvent is an oxo-compound.

5. The process according to claim 1, wherein the aprotic solvent is selected from the group consisting of N-methylpyrrolidone, dichloromethane, tetrahydrofuran (THF), ethyl acetate (EtOAc), acetone, methyl ethyl ketone, methyl isobutyl ketone, N, N-dimethylformamide (DMF), acetonitrile (MeCN), dimethyl sulfoxide (DMSO), propylene carbonate (PC), dioxane, and cyclohexanone; or mixtures thereof.

6. The process according to claim 1, wherein the glycolaldehyde dimer is biobased.

7. The process according to claim 1, wherein the oxidizing agent is selected from the group consisting of Dess-Martin periodinane, peracetic acid, oxygen, hydrogen peroxide, Oppenauer oxidation catalyst, metallo silicates, Shvo's catalyst, and aluminum isopropoxide; or mixtures thereof.

8. The process according to claim 1, wherein the oxidation step is conducted at a temperature in the range of from 0-100 ° C.

9. The process according to claim 1, wherein the oxidation step is conducted as a continuous process.

10. The process according to claim 2, wherein the reaction mixture has a pH which is kept in the range of from 6 to 8.

11. The process according to claim 1, wherein the glycolide is recovered.

* * * * *